US008119835B2

(12) United States Patent
Kalvinsh et al.

(10) Patent No.: US 8,119,835 B2
(45) Date of Patent: Feb. 21, 2012

(54) METHOD FOR PREPARATION OF 6-[3-(1-ADAMANTYL)-4-METHOXY-PHENYL]-2-NAPHTOIC ACID

(75) Inventors: Ivars Kalvinsh, Ikskile (LV); Aleksandrs Chernobrovijs, Olaine (LV); Vyacheslav Tribulovich, Sankt-Peterburg (RU); Vladimir Labeish, Sankt-Peterburg (RU)

(73) Assignee: JSC Grindeks, Riga (LV)

( * ) Notice: Subject to any disclaimer, the term of this patent is extended or adjusted under 35 U.S.C. 154(b) by 0 days.

(21) Appl. No.: 12/448,672

(22) PCT Filed: Dec. 28, 2007

(86) PCT No.: PCT/EP2007/064643
§ 371 (c)(1),
(2), (4) Date: Oct. 29, 2009

(87) PCT Pub. No.: WO2008/086942
PCT Pub. Date: Jul. 24, 2008

(65) Prior Publication Data
US 2010/0076219 A1    Mar. 25, 2010

(30) Foreign Application Priority Data
Dec. 28, 2006   (LV) .................................. P-06-149

(51) Int. Cl.
*C07C 63/34*   (2006.01)
*C07C 69/76*   (2006.01)
(52) U.S. Cl. .......................................... 562/467; 560/56
(58) Field of Classification Search .................. None
See application file for complete search history.

(56) References Cited

U.S. PATENT DOCUMENTS

| | | | |
|---|---|---|---|
| 6,031,127 A | 2/2000 | Yamamoto et al. | |
| 2004/0097566 A1* | 5/2004 | Pfahl et al. | 514/369 |
| 2006/0229465 A1* | 10/2006 | Castaldi et al. | 560/56 |
| 2007/0078189 A1* | 4/2007 | Sarshar | 514/690 |

FOREIGN PATENT DOCUMENTS

| | | |
|---|---|---|
| EP | 1707555 | 10/2006 |
| EP | 1707555 A1 * | 10/2006 |
| WO | WO 99/10292 | 3/1999 |
| WO | WO 2005/108338 | 11/2005 |

OTHER PUBLICATIONS

Anderson N., A Modified in Situ Suzuki Cross-Coupling of Haloarenes for the Preparation of C2-Symmetric Biaryls, J. Org. Chem. 1996, 61, 9556-9559.*
Gooben L., Pd-catalyzed synthesis of arylacetic acid derivatives from boronic acids, Chem. Commun., 2001, 669-670.*
Brimble M., Synthesis of a Dimeric Pyranonaphthoquinone via a Novel Double Furofuran Annulation Strategy, Tetrahedron Letters, 1998, 39, 5647-5650.*
Benbow J., Biaryl Formation Using the Suzuki Protocol: Considerations of Base, Halide, and Protecting Group, Tetrahedron Letters, 1996, vol. 37, No. 49, pp. 8829-8832.*
Percec V, Aryl Mesylates in Metal Catalyzed Homocoupling and Cross-Coupling Reactions. 2. Suzuki-Type Nickel-Catalyzed Cross-Coupling of Aryl Arenesulfonates and Aryl Mesylates with Arylboronic Acids, J. Org. Chem. 1995, 60, 1060-1065.*
Miyaura N., Palladium-Catalyzed Cross-Coupling Reactions of Organoboron Compounds, Chem. Rev. 1995, 95,2457-2483.*
International Preliminary Report on Patentability for International Application No. PCT/EP2007/064643, Jun. 30, 2009.
Ishiyama, et al., J. Org. Chem., 1995, 60, 7508-7510.
Kotha, et al., Tetrahedron, 2002, 58, 9633-9695.

* cited by examiner

*Primary Examiner* — Daniel Sullivan
*Assistant Examiner* — Jennifer C Sawyer
(74) *Attorney, Agent, or Firm* — Hueschen and Sage

(57) ABSTRACT

A method for preparation of 6-[3-(1-adamantyl)-4-methoxyphenyl]-2-naphthoic acid is disclosed based on "one pot" synthesis approach including a direct synthesis of boronic acid derivative from 2-(1-adamantyl)-4-bromoanisole and cycloboranes with a subsequent Suzuki-Miyaura coupling with 6-halonaphtenoates and basic hydrolysis of the reaction product in ethylene glycol or 1,2-propanediol.

13 Claims, No Drawings

METHOD FOR PREPARATION OF 6-[3-(1-ADAMANTYL)-4-METHOXYPHENYL]-2-NAPHTOIC ACID

The present invention relates to a method for preparation of 6-[3-(1-adamantyl)-4-methoxyphenyl]-2-naphthoic acid (adapalene). Adapalene is used for treating acne vulgaris [Waugh, J.; Noble, S.; Scott, L. Spotlight on adapalene in acne vulgaris. J. Am. J. Clin. Dermatol. 2004, 5 (5), 369-371; Jain, S. Topical tretinoin or adapalene in acne vulgaris: an overview. J. Dermatol. Treat. 2004, 15 (4), 200-207.] This substance also possesses antitumour activity [WO 2001/056563, Galderma Research (USA)]. Therefore a convenient method for manufacturing of adapalene is desirable.

A method for manufacturing 6-[3-(1-adamantyl)-4-methoxyphenyl]-2-naphthoic acid is known since 1986 [Shroot, B.; Eustache, J.; Bernardon, J.-M. EP 199636; Bezonaphtalene derivatives and compositions. U.S. Pat. No. 4,717,720 (1988)]. It is a multi-step process, involving the following steps:

a) alkylation of 4-bromophenol with adamantanol-2 to yield 2-(1-adamantyl)-4-bromophenol;
b) O-alkylation of 2-(1-adamantyl)-4-bromophenol with MeI to yield 2-(1-adamantyl)-4-bromoanisole;
c) preparation of Grignard's reagent from 2-(1-adamantyl)-4-bromoanisole, transformation thereof into a zinc derivative and its Ni-catalyzed condensation with methyl 6-bromo-2-naphtenoate to yield methyl-6-[3-(1-adamantyl)-4-methoxyphenyl]-2-naphtenoate;
d) basic hydrolysis of methyl-6-[3-(1-adamantyl)-4-methoxyphenyl]-2-naphtenoate to yield 6-[3-(1-adamantyl)-4-methoxyphenyl]-2-naphthoic acid.

This process has a number of shortcomings:
1) purification of 2-(1-adamantyl)-4-bromoanisole and methyl-6-[3-(1-adamantyl)-4-methoxyphenyl]-2-naphtenoate requires using column chromatography;
2) preparation of Grignard's reagent from 2-(1-adamantyl)-4-bromoanisole, transformation thereof into a zinc derivative and its Ni-catalyzed condensation with methyl 6-bromo-2-naphtenoate to yield methyl-6-[3-(1-adamantyl)-4-methoxyphenyl]-2-naphtenoate in step (c) is difficult to control on industrial scale and does not give stable yields.

In 2006 a process was published (Castaldi, G.; Allegrini, P.; Razezetti, G.; Ercoli, M.; A process for the preparation of adapalene, EP 1707555 A), using for the synthesis of adapalene an already known (Zim, D.; Lando, V. R.; Dupont, J.; Montiero, A. L. Org. Lett. 2001, 3, 3049) version of the Suzuki-Miyaura reaction for condensing 3-(1-adamantyl)-4-methoxyphenylboronic acid with tosyloxy-2-naphtenoate

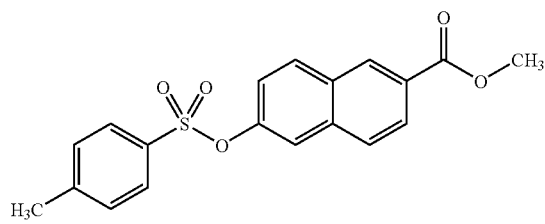

in presence of a Ni(II) salt and phosphine ligands.

A shortcoming of this method is the necessity to use 3-(1-adamantyl)-4-methoxyphenylboronic acid, prepared either via a Grignard's reagent or a Li derivative [Sarshar, S. Novel therapeutic agents for the treatment of cancer, metabolic diseases and skin disorders. WO 2005/108338 A1]).

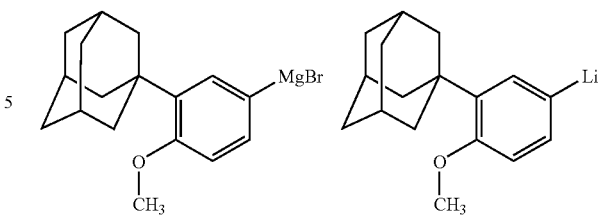

Therefore the objective of this invention was to develop an alternative process based on Suzuki-Miyaura reaction for preparation of 6-[3-(1-adamantyl)-4-methoxyphenyl]-2-naphthoic acid characterized by stable and high yields, easily scaleable and suitable for industrial application.

Since the most important and difficult in preparation intermediate in the synthesis of 6-[3-(1-adamantyl)-4-methoxyphenyl]-2-naphthoic acid is 3-(1-adamantyl)-4-methoxyphenylboronic acid it was necessary to develop a process where the derivatives of said boronic acid could be prepared in situ without using organomagnesium or organolithium intermediates. It would surmount the main disadvantage of the previously known methods for preparing of 3-(1-adamantyl)-4-methoxyphenylboronic acid derivatives, i.e., the problems of using organometallic compounds in the industrial processes.

We have unexpectedly discovered that differently from the known methods 3-(1-adamantyl)-4-methoxyphenylboronic acid derivatives can be prepared from 2-(1-adamantyl)-4-haloanisole by a direct catalytic heterofunctionalization reaction with pinacol borane, bispinacolatodiborane or other suitable cyclic alkylboranes in presence of Pd(0)-phosphine complex.

Therefore according to the present invention it is no more necessary to prepare, standardize and store as intermediate an 4-organometallic derivative of 2-(1-adamantyl)anisole that always poses a certain problem on industrial scale.

Further we have surprisingly discovered that the pinacol ester of 3-(1-adamantyl)-4-methoxyphenylboronic acid can be used in the next step, i.e., coupling according to Suzuki-Miyaura without separation from the reaction mixture. We have now discovered that it is not necessary to separate these derivatives of 3-(1-adamantyl)-4-methoxyphenylboronic acid from the reaction mixture but that they can be brought into the coupling reaction with 6-halo-2-naphtenoate or 6-tosyloxy-2-naphtenoate in presence of a catalytic complex of Pd(0)-phosphine in an "one pot" process.

It is preferable to use such catalyst that can be prepared in situ, e.g., from tris(dibenzylydeneacetone)dipalladium(0) [$Pd_2(dba)_3$] and 2-dicyclohexylphosphino-2',6'-dimethoxybiphenyl (Sphos).

We have now further discovered that a number of different acyclic and cyclic boranes are applicable for this process, the preferred ones being the easily available bis-pinacolatodiborane or pinacol borane:

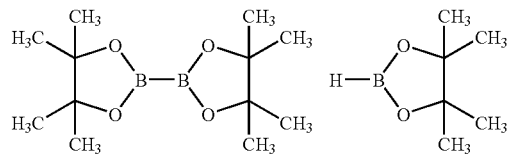

Therefore it is possible to introduce into the coupling reaction various derivatives of 3-(1-adamantyl)-4-methoxyphenylboronic acid, generated in situ, of general formula:

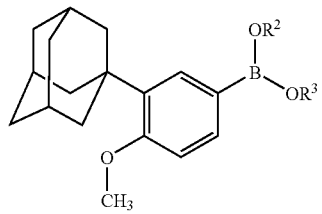

(IV)

wherein $R^2$ and $R^3$ together form a cycloalkyl, substituted cycloalkyl or —$CH_2OC_1$-$C_5$alkyl.

Excellent yields in this reaction are provided by various palladium-containing catalysts with Pd(0) with or without phosphine ligands like tetrakis(triphenylphosphine)palladium(0). As the most convenient sources of palladium Pd(0) palladium acetate and tris(dibenzylydeneacetone)-dipalladium(0) are useful.

Our investigations show that the following phosphine ligands are useful for the direct catalytic heterofunctionalization reaction in preparing 3-(1-adamantyl)-4-methoxyphenylboronic acid derivatives: 2-dicyclo-hexylphosphino-2',6'-dimethoxybiphenyl, 2-dicyclohexylphosphino-2'-methylbiphenyl, 2-dicyclo-hexylphosphino-2',6'-dimethylbiphenyl, 2-2-dicyclohexylphosphinobiphenyl, 2-di-tert-butylphosphino-2'-methyl-biphenyl, 2-di-tert-butylphosphino-2',6'-dimethyldiphenyl, 2-di-tert-butyl-phosphinobiphenyl, 2,4,6-tri-iso-propyl-2'-diphenylylphosphino-biphenyl, diphenylphosphinoferrocene, triphenylphosphine, tricyclohexylphosphine, as well as tri-tert-butylphosphine, although the best results are obtained using 2,2'-bis(diphenylphosphino)-diphenylether (DPEphos) as the ligand.

The amount of the catalyst is variable and it depends on the structure thereof and varies within the range of 0.0005 to 0.1 mol for mol of the used 3-(1-adamantyl)-4-haloanisole. In most cases the optimal concentration of the catalyst is about 0.005 mol for one mol of the anisole derivative. The reaction is realized in a suitable organic solvent like dioxan or in a mixture of organic solvents. The reaction temperature depends on the reactants and catalyst used and is between 20° C. and 100° C.

The present invention is explained but not limited by the following examples.

EXAMPLE 1

Step A. 2-(1-adamantyl)-4-bromoanisole

In a 1 L flask equipped with a stirrer, a reflux condenser and a dropping funnel, a mixture of 50 g (0.33 M) 1-adamantanol, 68 g (45.5 mL, 0.36 M) 4-bromoanisole and 500 mL of methylene chloride is prepared. The mixture is stirred until dissolved and then 35 g (19 mL, 0.36 M) sulfuric acid added during one hour. The reaction mixture is stirred for 4 hours, 200 mL of water added, stirred for another 10 min, transferred to separating funnel and the organic layer collected, which is neutralized by two portions of 100 mL 10% sodium carbonate solution. Methylene chloride is distilled off completely, the residue dissolved in 300 mL of ethyl acetate, filtered, concentrated to 200 mL and left to crystallize at 0° C. for 16 h. The crystals are filtered off, washed by 50 mL of cold ethyl acetate and dried at 100° C. for one hour. 2-adamantyl-4-bromoanisole, 76 g (72%) with m.p. 140-141° C. is obtained.

NMR (500 MHz, DMSO $D_6$)

δ: 1.75 (s, 6H), 2.03 (s, 9H), 3.81 (s, 3H), 6.82 (d, 1H, J=8 Hz), 7.17 (s, 1H), 7.23 (d, 1H, J=8 Hz).

Scaling the synthesis up 10 times did not change either the yield or quality of the 2-(1-adamantyl)-4-bromoanisole.

EXAMPLE 2

Step B. 3-(1-adamantyl)-4-methoxyphenylboronic acid pinacol ester

Into a 2 L double-necked flask equipped with a stirrer, a reflux condenser and a gas-inlet adapter is introduced 800 mL of dioxan, 100 g (0.31 M) of 2-(1-adamantyl)-4-bromoanisole, 94 g (130 mL, 0.93 M) of triethylamine, 3.5 g (0.0155 M, 5 mol %) of palladium acetate and 16.7 g (0.031 M, 10 mol %) of 2,2'-bis-(diphenylphosphino)diphenylether (DPEphos). The solution is stirred for 30 min and under a slight stream or argon 60 g (68 mL, 0.47 M) of pinacol borane solution in 300 mL of dioxan added. The reaction mixture is refluxed under stirring for 12 h, the solvent distilled off in vacuo at water-bath temperature of 60° C. The residue is dissolved in 500 mL of warm ethyl acetate, filtered and concentrated to 300 mL. The solution is left for 16 h at about 0° C. The precipitate is filtered off, washed with a minimal volume of cold ethyl acetate and dried at 80° C.

3-(1-Adamantyl)-4-methoxyphenylboronic acid pinacol ester, 71 g (62%) with m.p. 162-164° C. is obtained.

$^1$H NMR (500 MHz, DMSO $D_6$)

δ: 1.30 (s, 12H), 1.76 (s, 6H), 2.07 (s, 3H), 2.09 (s 6H), 3.85 (s, 3H), 6.83 (d, 1H, J=8 Hz), 7.49 (s, 1H), 7.50 (d, 1H, J=8 Hz).

Using as a ligand 2-dicyclohexylphosphino-2',6'-dimethoxybiphenyl (Sphos) instead of DPEphos does not substantially influence the yield of the final product.

The yield is also not influenced by replacing tris(dibenzylidene-acetone)dipalladium(0) ($Pd_2(dba)_3$) by palladium acetate as Pd(0) source.

EXAMPLE 3

Reaction is performed as in Example 2. As the ligand 12.7 g (0.031 M, 10 mol %) of 2-dicyclohexylphosphino-2',6'-dimethoxybiphenyl (Sphos) is used and 7.1 g (0.007 M, 5 mol %) of tris(dibenzylydeneacetone)-dipalladium(0) ($Pd_2(dba)_3$) is used as a source of Pd(0).

3-(1-Adamantyl)-4-methoxyphenylboronic acid pinacol ester, 70 g (61%) is obtained.

Using as a catalyst dichloropalladium 1,1'-bis(diphenylphosphino)-ferrocene [$PdCl_2(dppf)CH_2Cl_2$] causes a moderate drop in the yield of the end product.

EXAMPLE 4

Reaction is performed as described in Example 2. Dichloropalladium 1,1'-bis(diphenylphosphino)ferrocene, 12.6 g (5 mol %) is used as the catalyst.

3-(1-Adamantyl)-4-methoxyphenylboronic acid pinacol ester, 59 g (52%) is obtained.

If as the catalyst a freshly prepared tetrakis(triphenylphosphine)-palladium(0) Pd[P(Ph)$_3$]$_4$ is used, the yield of the end product drops considerably.

EXAMPLE 5

Reaction is performed as described in Example 2. As the catalyst a freshly prepared tetrakis(triphenylphosphine)palladium Pd[P(Ph)$_3$]$_4$ is used.

3-(1-Adamantyl)-4-methoxyphenylboronic acid pinacol ester, 9 g only (8%) is obtained.

Scaling the synthesis up 5 times under the optimal reaction conditions did not lower the yield and quality of the end product.

3-(1-adamantyl)-4-methoxyphenylboronic acid pinacol ester can also be prepared, using bispinacolatodiborane.

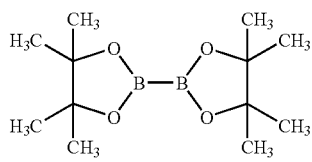

EXAMPLE 6

Into a 1 L double-necked flask equipped with a stirrer, a reflux condenser and a gas-inlet adapter is introduced 400 mL of dimethyl-formamide, 50 g (0.16 M) of 2-(1-adamantyl)-4-bromoanisole, 1.8 g (0.0078 M, 5 mol %) of palladium acetate, 6.4 g (0.0155 M, 10 mol %) of 2-dicyclohexylphosphino-2',6'-dimethoxybiphenyl (Sphos) and 51 g (0.2 M) of bispinacolatodiborane. The solution is stirred for 30 min under a slight stream of argon and then 49 g (0.5 M) of pulverized anhydrous potassium carbonate added. The reaction mixture is stirred at 90° C. under a slight stream of dry argon for 10 h. After completion the solvent is removed in vacuo at 70° C. in the water bath. The residue is dissolved in 200 mL of ethyl acetate. The solution is filtered hot, concentrated to 100 mL and left for 16 h at about 0° C. to crystallize. The precipitate is filtered off, washed by a minimal volume of cold ethyl acetate and dried at 80° C.

3-(1-Adamantyl)-4-methoxyphenylboronic acid pinacol ester, 28 g (48%) with m.p. 162-164° C. is obtained.

If instead of the palladium acetate a tris(dibenzylydeneacetone)-dipalladium(0) ($Pd_2(dba)_3$) is used no substantial change in the yield of 3-(1-adamantyl)-4-methoxyphenylboronic acid pinacol ester is observed.

EXAMPLE 7

Reaction is performed as in Example 6. As the source of Pd(0) to tris(dibenzylydeneacetone)dipalladium(0) ($Pd_2(dba)_3$) is used.

3-(1-Adamantyl)-4-methoxyphenylboronic acid pinacol ester, 29 g (49.5%) is obtained.

Using as the ligand dichloropalladium 1,1'-bis(diphenylphosphino)-ferrocene [$PdCl_2(dppf)CH_2Cl_2$] or 2,2'-bis(diphenylphosphino)diphenylether (DPEphos) does not cause a lower yield of the end product (gas chromatography data).

EXAMPLE 8

Reaction is performed as described in Example 6. Dichloropalladium 1,1'-bis(diphenylphosphino)ferrocene, 6.3 g (0.0078 M, 5 mol %) is used as the catalyst.

3-(1-Adamantyl)-4-methoxyphenylboronic acid pinacol ester, 28% (gas chromatography data) is obtained.

EXAMPLE 9

Reaction is performed as described in Example 6. As the ligand 2,2'-bis(diphenylphosphino)diphenylether (DPEphos), 8.4 g (0.0155 M, 10 mol %) is used.

3-(1-Adamantyl)-4-methoxyphenylboronic acid pinacol ester, 36% (gas chromatography data) is obtained.

Scaling the synthesis up 10 times under the optimal reaction conditions did not lower the yield and quality of the end product.

EXAMPLE 10

Step C. Catalytic coupling of 3-(1-adamantyl)-4-methoxyphenylboronic acid with 6-bromo-2-naphthoic acid ester according to Suzuki-Miyaura In a 1 L double-necked flask, equipped with a stirrer, a reflux condenser and a gas inlet adapter is introduced 0.25 g (0.5 mol %) of tris(dibenzylydeneacetone)dipalladium(0) $Pd_2(dba)_3$ and dissolved in 500 mL of tetrahydrofuran. Then 1 g (1 mol %) of 2-dicyclohexylphosphino-2',6'-dimethoxybiphenyl (Sphos) is added and the solution stirred for 30 min under a slight stream or argon.

To the reaction mixture 30 g (0.105 M) 3-(1-adamantyl)-4-methoxyphenylboronic acid and 25 g (0.094 M) methyl 6-bromo-2-naphtenoate is added and stirred until all components are dissolved. A solution of 30 g (0.28 M) of sodium carbonate in 150 mL of water is added. To complete the reaction, the mixture is vigorously stirred for 4 h with boiling under a slight stream of argon.

After the completion the reaction mixture is cooled to room temperature and filtered without separating the layers. The precipitate constitutes the main portion of the product. The rest of the product is obtained by concentrating the organic layer to ¼, cooling and filtering off the precipitate and combining with the main portion.

The raw product is dissolved in 200 mL of dimethylacetamide, filtered hot, reduced to about 150 mL and left for 16 h at room temperature to crystallize.

The voluminous crystals are filtered off and dried at 150-180° C. for 2 h. Methyl 6-[3-(1-adamantyl)-4-methoxyphenyl]-2-naphtenoate, 34 g (85%) with m.p. 222-225° C. is obtained.

$^1H$ NMR (500 MHz, DMSO

δ: 1.79 (s, 6H), 2.10 (s, 3H), 2.16 (s, 6H), 3.90 (s, 3H), 3.94 (s, 3H), 6.99 (d, 1H, J=8 Hz), 7.51 (s, 1H), 7.52 (d, 1H, J=8 Hz), 7.78 (d, 1H, J=9 Hz), 7.94 (d, 1H, J=9 Hz), 7.98-8.02 (m, 3H), 8.55 (s, 1H).

Increasing the concentration of the catalyst to 5 mol % shortens the reaction time to 0.5 h, but does not influence the yield of the end product. Reducing the quantity of the catalyst to 0.05 mol % leads to increase of reaction time to 16 hours and drops the yield of methyl 6-[3-(1-adamantyl)-4-methoxyphenyl]-2-naphtenoate to 76%.

Scaling up the synthesis 5 times under the optimal reaction conditions did not lower the yield and quality of methyl 6-[3-(1-adamantyl)-4-methoxyphenyl]-2-naphtenoate.

Methyl 6-[3-(1-adamantyl)-4-methoxyphenyl]-2-naphtenoate can be prepared without separation and purification of 3-(1-adamantyl)-4-methoxyphenylboronic acid pinacol ester.

EXAMPLE 11

Into a 3 L double-necked flask equipped with a stirrer, a reflux condenser and a gas-inlet adapter is introduced 800 mL of dioxan, 100 g (0.31 M) of 2-(1-adamantyl)-4-bromoanisole, 94 g (130 mL, 0.93 M) of triethylamine, 3.5 g (0.0155 M, 5 mol %) of palladium acetate and 12.7 g (0.031 M, 10 mol %) of 2-dicyclohexylphosphino-2',6'-dimethoxybiphenyl (Sphos).

The solution is stirred for 30 min under a slight stream or argon and then 51 g (58 mL, 0.4 M) of pinacol borane solution in 300 mL of dioxan added. The mixture is stirred for 12 h under a slight stream or argon.

The reaction mixture is cooled to room temperature, 61 g (0.23 M) of methyl 6-[3-(1-adamantyl)-4-methoxyphenyl]-2-naphtenoate added and then an in advance prepared solution of 127 g (1.2 M) of sodium carbonate in 600 mL of water is added.

The process is carried on for 4 h under vigorous stirring and reflux at 80° C. under a slow stream or argon.

After the completion the reaction mixture is cooled to room temperature and filtered without separating the layers. The precipitate constitutes the main portion of the product. The rest of the product is obtained by concentrating the organic layer to ¼, cooling and filtering off the precipitate.

The combined portions of the end product are dissolved in 200 mL of dimethylacetamide, filtered hot, concentrated to 150 mL and left at a room temperature for 16 h to crystallize. The crystals are filtered off and dried at 150-180° C. for 2 h.

Methyl 6-[3-(1-adamantyl)-4-methoxyphenyl]-2-naphtenoate, yield 78 g, 59% based on the starting 2-(1-adamantyl)-4-bromoanisole. The purity of the end product exceeds 99%.

Scaling the synthesis 10 times does not lower the yield and quality of the end product.

"One pot" preparation of methyl-6-[3-(1-adamantyl)-4-methoxyphenyl]-2-naphtenoate from 2-(1-adamantyl)-4-bromoanisole

EXAMPLE 12

Into a 3 L double-necked flask equipped with a stirrer, a reflux condenser and a gas-inlet adapter is introduced 800 mL of dioxan, 100 g (0.31 M) of 2-(1-adamantyl)-4-bromoanisole, 94 g (130 mL, 0.93 M) of triethylamine, 3.5 g (0.0155 M, 5 mol %) of palladium acetate and 12.7 g (0.031 M, 10 mol %) of 2,2'-bis-(diphenylphosphino)diphenylether (DPEphos).

The solution is stirred for 30 min under a slight stream or argon and then 51 g (58 mL, 0.4 M) of pinacol borane solution in 300 mL of dioxan added. Reaction mixture is refluxed for 12 h under a slight stream or argon. The reaction mixture is cooled to room temperature, 61 g (0.23 M) of methyl-6-[3-(1-adamantyl)-4-methoxyphenyl]-2-naphtenoate added and then a solution of 127 g (1.2 M) of sodium carbonate in 600 mL of water is added. The reaction mixture is vigorously stirred at 80° C. for 4 h under a stream of argon, cooled to 20° C. and the product filtered off. The filtrate is concentrated to ¼ and cooled. The precipitate is filtered off, the combined portions of the end product are dissolved in 200 mL of dimethylacetamide, filtered hot, concentrated to 150 mL and left at a room temperature for 16 h to crystallize. The crystals are filtered off and dried at 150-180° C. 78-112 g of methyl 6-[3-(1-adamantyl)-4-methoxyphenyl]-2-naphtenoate with purity over 99% are obtained (yield 59-85% from 2-(1-adamantyl)-4-bromoanisole).

Scaling up the synthesis 3 times the yield and purity of the end product is not changed.

EXAMPLE 13

Step D: Basic hydrolysis of methyl-6-[3-(1-adamantyl)-4-methoxyphenyl]-2-naphtenoate Into a 600 mL beaker is introduced 10 g of methyl-6-[3-(1-adamantyl)-4-methoxyphenyl]-2-naphtenoate, 300 mL of ethylene glycol and heated almost to boiling. The obtained clear solution is added 15 g of sodium hydroxide in 3 portions and vigorously stirred for 20 min.

The hot reaction mixture is slowly added with vigorous stirring to a cold 5% solution of aqueous hydrochloric acid.

The suspension thus obtained is stirred for 30 min and filtered off. The precipitate is pressed on filter, washed with 3×500 mL of hot water and dried at 100° C. for 16 h. 6-[3-(1-adamantyl)-4-methoxyphenyl]-2-naphthoic acid, 9.3 g (96%) with m.p. 320° C. and purity over 97% is obtained.

NMR (500 MHz, DMSO

δ: 1.79 (s, 6H), 2.10 (s, 3H), 2.16 (s, 6H), 3.90 (s, 3H), 6.99 (d, 1H, J=8 Hz), 7.51 (s, 1H), 7.52 (d, 1H, J=8 Hz), 7.76 (d, 1H, J=9 Hz), 7.92 (d, 1H, J=9 Hz), 7.98-8.02 (m, 3H), 8.55 (s, 1H), 12.7 (s, 1H).

Using 1,2-propanediol instead of ethylene glycol the concentration of the hydrolyzed methyl 6-[3-(1-adamantyl)-4-methoxyphenyl]-2-naphtenoate in solution can be increased by 50%.

EXAMPLE 14

Into a 600 mL beaker is introduced 15 g of methyl 6-[3-(1-adamantyl)-4-methoxyphenyl]-2-naphtenoate, 300 mL of 1,2-propanediol and heated almost to boiling. To the obtained clear solution is added 15 g of sodium hydroxide in 3 portions and vigorously stirred for 20 min. Further operations for treating the reaction mixture and separation of the end product are similar to that of Example 13. The yield of 6-[3-(1-adamantyl)-4-methoxyphenyl]-2-naphthoic acid is 96%.

Scaling up the synthesis under the optimal reaction conditions did not lower the yield and quality of the end product.

Thus the disclosed method for preparation of 6-[3-(1-adamantyl)-4-methoxyphenyl]-2-naphthoic acid from 2-(1-adamantyl)-4-haloanisole is characterized by stable and high yields, simple "one pot" technology and is easily realized in pharmaceutical manufacturing.

The invention claimed is:

1. A method for preparation of a compound of formula (I)

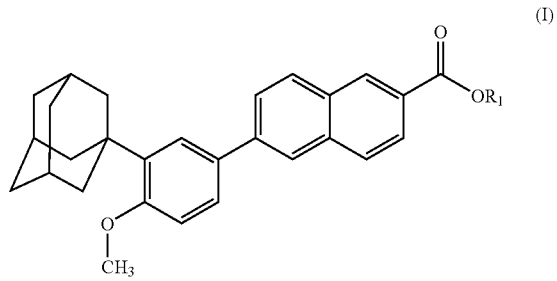

wherein:
$R_1$ is selected from the group consisting of K, Na, Li, H, straight $C_1$-$C_{10}$alkyl, branched $C_3$-$C_{10}$alkyl or cyclic$C_3$-$C_{10}$alkyl and $CH_2OC_1$-$C_5$alkyl,
from a compound of formula (II)

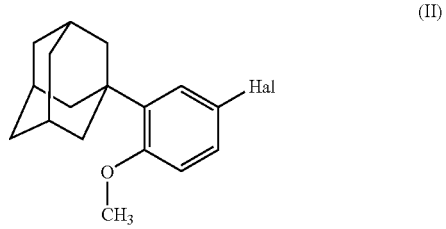

wherein:

Hal is selected from the group consisting of Cl, Br and I, by reacting with a compound of formula (III)

(III)

wherein:

R$^1$ and R$^2$ independently of each other are selected from the group consisting of K, Na, Li, H, aryl, straight C$_1$-C$_{10}$alkyl, branched C$_3$-C$_{10}$alkyl and cyclic C$_3$-C$_{10}$alkyl, or R$^1$ and R$^2$ together form a group —(CR$^4$R$^5$)$_m$—, —(CR$^6$R$^7$)$_n$—, wherein R$^4$, R$^5$, R$^6$ and R$^7$ independently of each other are selected from the group consisting of aryl, H, straight C$_1$-C$_5$alkyl, branched C$_3$-C$_5$alkyl and cyclic C$_3$-C$_5$alkyl; and m and n independently of each other are 1 or 2, or R$^1$ and R$^2$ together form ortho-substituted aryl, R$^3$ is selected from the group consisting of H and

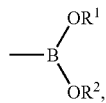

in an inert solvent in presence of a basic agent and a catalyst selected from the group consisting of a palladium catalyst, Pd(0) and Pd(0)-phosphine ligand complex, wherein the product of the reaction between the compound of formula (II) and the compound of formula (III) is not isolated and is further reacted with a compound (IV)

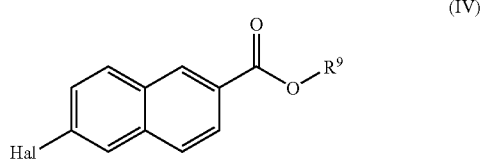
(IV)

wherein:

R$^9$ is selected from the group consisting of K, Na, Li, H, aryl, straight C$_1$-C$_{10}$alkyl, branched C$_3$-C$_{10}$alkyl, cyclic C$_3$-C$_{10}$alkyl, and CH$_2$OC$_1$-C$_5$alkyl;

Hal is selected from the group consisting Cl, Br and I, in the same reaction mixture, with or without addition of an inorganic base.

2. The method of claim 1, wherein the source of Pd(0) is selected from the group, consisting of palladium acetate and tris(dibenzylydene-acetone)dipalladium(0).

3. The method of claim 2, wherein the phosphine ligand is selected from the group consisting of 2-dicyclohexyphosphino-2',6'-dimethoxybiphenyl, 2-dicyclohexylphosphino-2'-methylbiphenyl, 2-dicyclo-hexylphosphino-2',6'-dimethylbiphenyl, 2-2-dicyclohexylphosphino-biphenyl, 2-di-tert-butylphosphino-2'-methylbiphenyl, 2-di-tert-butylphosphino-2',6'-dimethylbiphenyl, 2-di-tert-butylphosphinobiphenyl, 2,4,6-tri-iso-propyl-2'-diphenylylphosphinobiphenyl, diphenylphosphinoferro-cene, triphenyl-phosphine, tricyclohexylphosphine, tri-tert-butylphosphine, and 2-dicyclohexylphosphino-2',6'-dimethoxybiphenyl.

4. The method of claim 3, wherein the phosphine ligand is 2-dicyclohexylphosphino-2',6'-dimethoxybiphenyl.

5. The method of claim 1, where the phosphine ligand is one or more than one used simultaneously.

6. The method of claim 1, wherein the basic agent is selected from the group consisting of N(R$^{10}$R$^{11}$R$^{12}$), wherein R$^{10}$, R$^{11}$ and R$^{12}$ independently of each other are selected from the group consisting of aryl, straight C$_1$-C$_{10}$alkyl, branched C$_3$-C$_{10}$alkyl and cyclic C$_3$-C$_{10}$alkyl, potassium and sodium acetate.

7. The method of claim 1, wherein the ratio of the basic agent and compound (II) is from 1 to 3 mol to mol.

8. The method of claim 1, wherein the inert solvent is selected from the group consisting of tetrahydrofuran, tert-butylmethylether, dimethoxy-ethane, dioxane, benzene, toluene, xylene, dimethylformamide and combinations thereof.

9. The method of claim 1, wherein the reaction is performed in the presence of an organic solvent or a mixture thereof or a mixture of organic solvent with water.

10. The method of claim 1, wherein as the additional basic agent an inorganic base is used which is selected from the group consisting of sodium and potassium carbonates, acetates and phosphates.

11. The method of claim 1, wherein the ratio of the palladium catalyst and compound (II) is from 0.005 to 0.2 mol to mol.

12. The method of claim 1, wherein the reaction is performed at a temperature from about 20° C. to about 100° C.

13. The method of claim 1, wherein Hal is Br.

* * * * *